(12) United States Patent
Yoshida et al.

(10) Patent No.: US 6,784,191 B2
(45) Date of Patent: Aug. 31, 2004

(54) BENZAMIDINE DERIVATIVES

(75) Inventors: Kaoru Yoshida, Kawasaki (JP);
Tadakiyo Nakagawa, Kawasaki (JP);
Takashi Kayahara, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/164,623

(22) Filed: Jun. 10, 2002

(65) Prior Publication Data

US 2002/0193348 A1 Dec. 19, 2002

Related U.S. Application Data

(63) Continuation of application No. PCT/JP00/08656, filed on Dec. 7, 2000.

(30) Foreign Application Priority Data

Dec. 8, 1999 (JP) .......................................... 11-348504

(51) Int. Cl.[7] ...................... A61K 31/445; C07D 401/04
(52) U.S. Cl. ..................... 514/318; 514/231.2; 514/327; 514/423; 544/106; 546/22; 546/193; 548/413
(58) Field of Search .............................. 514/231.2, 318, 514/327, 423; 544/106; 546/22, 193; 548/413

(56) References Cited

U.S. PATENT DOCUMENTS

| | | | | |
|---|---|---|---|---|
| 5,952,307 | A | 9/1999 | Powers et al. .................. | 514/19 |
| 6,410,538 | B2 * | 6/2002 | Nakagawa et al. .... | 514/252.01 |
| 2002/0107290 | A1 * | 8/2002 | Nakagawa et al. ......... | 514/619 |

FOREIGN PATENT DOCUMENTS

| | | |
|---|---|---|
| EP | 1 236 712 | 9/2002 |
| WO | 99/31661 | 7/1998 |
| WO | 99/64392 | 12/1999 |

OTHER PUBLICATIONS

Wyngaarden et al. "Cecil textbook of medicine" p. 2066, 2070 (1983).*
Patent Abstracts of Japan, JP 11–140040, May 25, 1999.
Li, Min et al., "Structure–based design and synthesis of novel thrombin inhibitors based on phosphinic piptide mimetics", Bioorg. Med. Chem. Lett., 1999, vol. 9, No. 14, pp. 1957–1962.

* cited by examiner

*Primary Examiner*—Celia Chang
(74) *Attorney, Agent, or Firm*—Oblon, Spivak, McClelland, Maier & Neustadt, P.C.

(57) ABSTRACT

A benzamidine derivative of the following formula, analogs thereof and pharmaceutically acceptable salts thereof have an effect of inhibiting the blood coagulation based on their excellent effect of inhibiting activated blood-coagulation factor X. Thus, a blood-coagulation inhibitor or an agent for preventing or treating thrombosis or embolism, containing one of those compounds as the active ingredient, is provided.

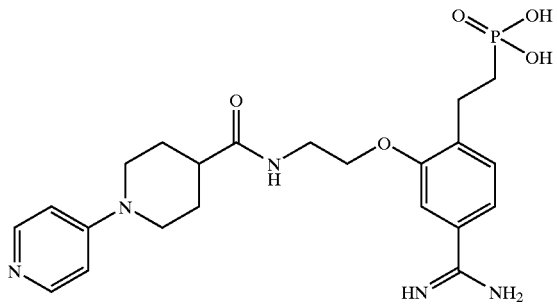

30 Claims, No Drawings

BENZAMIDINE DERIVATIVES

CROSS-REFERENCE TO RELATED APPLICATIONS

This application is a continuation of International Application PCT/JP00/08656, filed on Dec. 7, 2000, which claims priority to Japanese Patent Application No. 11-348504, filed on Dec. 8, 1999, both of which are incorporated by reference herein in their entireties.

BACKGROUND OF THE INVENTION

The present invention relates to new benzamidine derivatives which can be orally administrated to exhibit a strong anticoagulant effect by reversibly inhibiting activated blood-coagulation factor X; anticoagulants containing them as active ingredients; and agents for preventing or treating diseases caused by thrombi or emboli. These diseases include, for example, cerebrovascular disorders such as cerebral infarction, cerebral stroke, cerebral thrombosis, cerebral embolism, transient ischemic attack (TIA) and subarachnoidal hemorrhage (vasospasm); ischemic heart diseases such as acute and chronic myocardial infarction, unstable angina and coronary thrombolysis; pulmonary vascular disorders such as pulmonary infarction and pulmonary embolism; peripheral occlusion; deep vein thrombosis; disseminated intravascular coagulation; thrombus formation after an artificial blood vessel-forming operation or artificial valve substitution; re-occlusion and re-stenosis after a coronary bypass-forming operation; re-occlusion and re-stenosis after reconstructive operation for the blood circulation such as percutaneous transluminal coronary angioplasty (PTCA) or percutaneous transluminal coronary recanalization (PTCR); and thrombus formation in the course of the extracorporeal circulation.

As the habit of life is being westernized and people of advanced ages are increasing in Japan, thrombotic and embolismic patients such as those suffering from myocardial infarction, cerebral thrombosis and peripheral thrombosis are increasing in number year by year, and the treatment of patients with these diseases is becoming more and more important in the society. Anticoagulation treatment is included in the internal treatments for the remedy and prevention of thrombosis, like fibrinolytic therapy and anti-platelet therapy.

Thrombin inhibitors were developed as thrombus-formation inhibitors in the prior art. However, it has been known that since thrombin not only controls the activation of fibrinogen to form fibrin, which is the last step of the coagulation reaction, but also deeply relates to the activation and aggregation of blood platelets, the inhibition of the action of thrombin causes a danger of causing hemorrhage. In addition, when thrombin inhibitors are orally administered, the bioavailability thereof is low. At present, no thrombin inhibitors which can be orally administered is available on the market.

Since the activated blood coagulation factor X is positioned at the juncture of an extrinsic coagulation cascade reaction and an intrinsic coagulation cascade reaction and in the upstream of thrombin, it is possible to inhibit the coagulation system more efficiently and specifically, than the thrombin inhibition, by inhibiting the factor X (Tidwell, R.; Webster, W, P.; Shaver, S. R.; Geratz, J. D. THROMBOSIS RESEARCH, Vol. 19, pages 339 to 349; 1980).

Benzamidine derivatives capable of selectively inhibiting activated blood coagulation factor X have been disclosed until now (see, for example, WO 9831661 and WO 9964392). However, it is eagerly demanded to further develop a medicine having a more excellent effect of inhibiting activated blood coagulation factor X and also an excellent effect of inhibiting the blood coagulation.

DISCLOSURE OF THE INVENTION

The object of the present invention is to provide compounds having an excellent effect of inhibiting the effect of activated blood coagulation factor X.

Another object of the present invention is to provide compounds having an effect of specifically inhibiting the effect of activated blood coagulation factor X, which can be orally administered.

Still another object of the present invention is to provide a blood-coagulation inhibitor or an agent for preventing or treating thrombosis or embolism, which contains one of the above-described compounds.

A further object of the present invention is to provide agents, containing one of the above-described compounds, for preventing and treating diseases caused by cerebrovascular disorders, diseases caused by ischemic heart diseases, diseases caused by pulmonary vascular disorders, peripheral embolism, deep vein thrombosis, disseminated intravascular coagulation, thrombus formation after an artificial blood vessel-forming operation or artificial valve substitution, re-occlusion and re-stenosis after a coronary bypass-forming operation, re-occlusion and re-stenosis after reconstructive operation for the blood circulation, and thrombus formation in the course of the extracorporeal circulation.

Another object of the present invention is to provide a pharmaceutical composition containing an above-described compound(s).

After intensive investigations made under these circumstances, the inventors have found that specified new benzamidine derivatives having a phosphonoethyl group have an excellent effect of inhibiting activated blood coagulation factor X and are usable for preventing and treating various diseases caused by thrombi and emboli. The present invention has been completed on the basis of this finding. For example, a compound of formula (2-1) given below has an effect of selectively inhibiting activated blood coagulation factor X. Namely, this compound has an excellent effect of inhibiting activated blood coagulation factor X (pIC50= 8.5), while it has no activity of inhibiting thrombin (pIC50= <3.5).

In addition, the compound of formula (2-1) also exhibited a high activity of inhibiting the blood coagulation (pPT2= 6.8).

Namely, the present invention provides benzamidine derivatives of following general formula (1) or pharmaceutically acceptable salts thereof, and blood coagulation inhibitors containing them as the active ingredients:

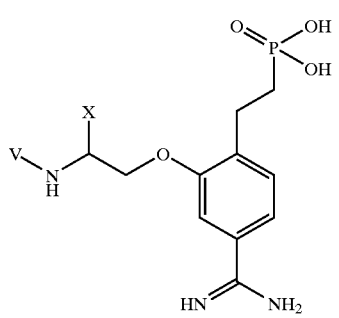

(1)

wherein X represents a hydrogen atom, a carboxyl group, an alkoxycarbonyl group having 2 to 4 carbon atoms, an alkyl group having 1 to 3 carbon atoms, which may have a substituent(s), or a benzyl group which may have a substituent(s); the substituent(s) being a carboxyl group or alkoxycarbonyl groups having 2 to 8 carbon atoms, and V represents a benzoyl or piperidinecarbonyl group which may have a substituent(s); the substituent(s) being selected from the group consisting of iminoalkylpiperidyloxy groups having 7 to 10 carbon atoms, aryl groups having 6 to 10 carbon atoms, heteroaryl groups having 4 to 5 carbon atoms, carbamoyl group, and mono- and dialkylcarbamoyl groups having 2 to 7 carbon atoms.

BEST MODE FOR CARRYING OUT THE INVENTION

In this specification, the alkyl groups, and also the alkyl groups in the alkoxycarbonyl groups, iminoalkylpiperidyloxy groups, etc. may be branched or may have a ring(s). The alkyl groups are, for example, those having 1 to 6 carbon atoms, preferably 1 to 5 carbon atoms, such as methyl group, ethyl group, propyl group, isopropyl group and cyclopropyl group. The alkoxycarbonyl groups are, for example, those having 2 to 10 carbon atoms, preferably 2 to 8 carbon atoms, such as methoxycarbonyl group, ethoxycarbonyl group, propyloxycarbonyl group and benzyloxycarbonyl group. The iminoalkylpiperidyloxy groups are, for example, those having 7 to 10 carbon atoms such as 1-acetimidoyl-4-piperidyloxy group.

In this specification, the aryl groups are, for example, phenyl group, 1-naphthyl group and 2-naphthyl group; and the heteroaryl groups are preferably aromatic heterocyclic groups containing 1 or 2 hetero atoms selected from the group consisting of nitrogen atom, oxygen atom and sulfur atom, such as pyridyl group, pyrimidyl group, pyridazinyl group and pyrazinyl group.

In this specification, the two alkyl groups in each of the dialkylcarbamoyl groups may be bonded to each other to form a ring. In this case, methylene group may be replaced with oxygen atom, amino group or sulfur atom to form 1-pyrrolidinecarbonyl group, 1-piperidinecarbonyl group, 1-piperazinecarbonyl group, 1-morpholinecarbonyl group, etc.

In general formula (1), the group represented by X is preferably hydrogen atom, carboxymethyl group or carboxyethyl group.

The group represented by V is benzoyl or piperidinecarbonyl group which may have a substituent(s). Preferred substituents are iminoalkylpiperidyloxy groups having 7 to 10 carbon atoms, aryl groups having 6 to 10 carbon atoms, heteroaryl groups having 4 or 5 carbon atoms, carbamoyl group and mono- or dialkylcarbamoyl groups having 2 to 7 carbon atoms. In those groups represented by V, preferred groups are 1-acetimidoyl-4-piperidyloxybenzoyl group, 1-(4-pyridyl)-piperidine-4-carbonyl group and 4-(1-pyrrolidinecarbonyl)benzoyl group.

Compounds of the following formulae (2-1) to (2-6) and pharmaceutically acceptable salts of them are preferred:

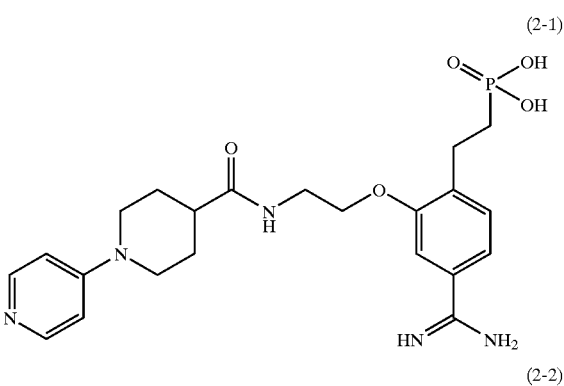

(2-1)

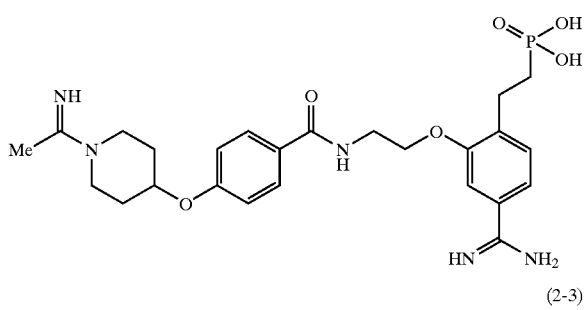

(2-2)

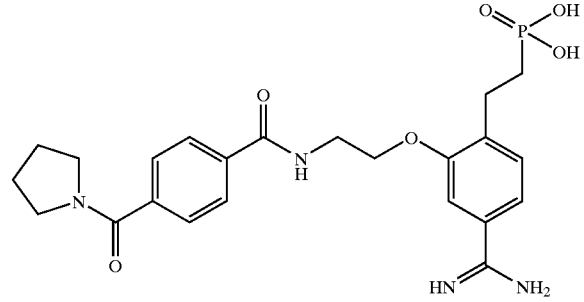

(2-3)

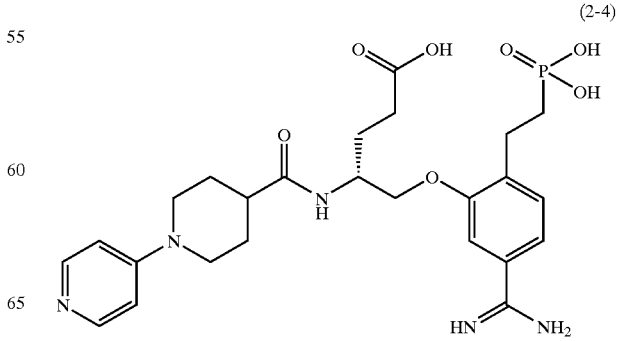

(2-4)

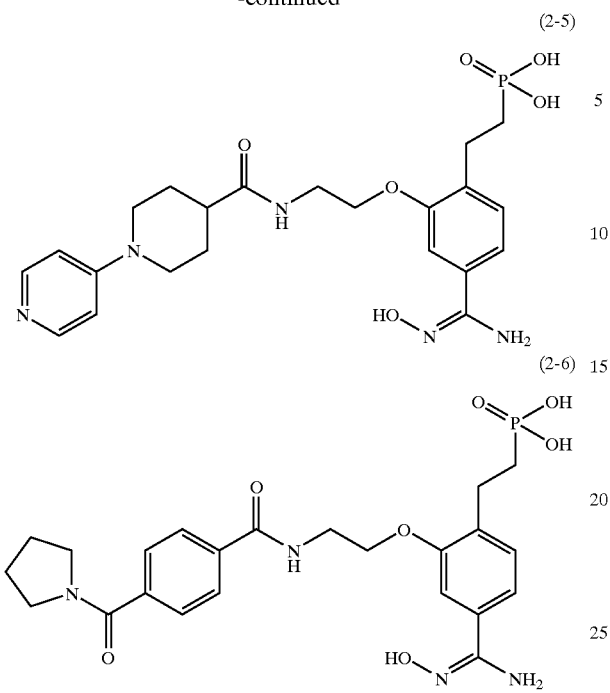

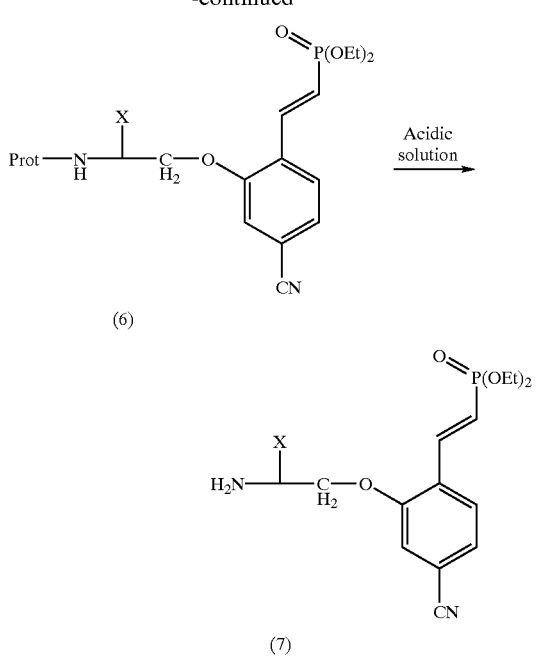

The benzamidine derivatives (1) of the present invention can be produced by processes described below. For example, compounds of general formula (1—1) can be produced as described below.

Namely, an iodobenzonitrile derivative (5) can be obtained by reacting an aminoalkyl halide (3), in which nitrogen is protected with benzyloxycarbonyl group or t-butoxycarbonyl group, with 3-hydroxy-4-iodobenzonitrile (4) in the presence of a base such as potassium carbonate in a solvent such as dimethylformamide. A phosphoric acid diester derivative (6) can be derived from the obtained iodobenzonitrile derivative (5) by, for example, Heck reaction in dimethylformamide or the like as the solvent. The protecting group on the nitrogen of the obtained phosphoric acid diester derivative (6) can be removed in, for example, an acidic solution such as 4 N solution of hydrogen chloride in dioxane to obtain an amine (7).

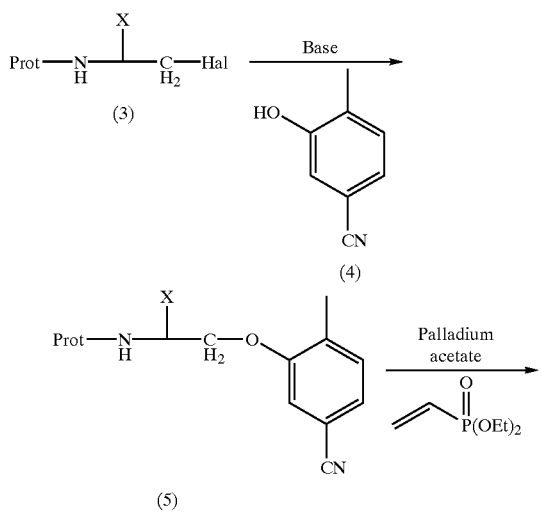

Prot in the above formula represents a protecting group such as Boc group or Z group, and Hal represents a halogen atom.

Then the amine (7) is reacted with a condensing agent in the presence of a base such as triethylamine in a solvent such as dimethylformamide. The amine can be thus converted into an amide (8) by condensing it with a carboxylic acid. Cyano group in the amide (8) obtained as described above can be converted into amidino group to obtain an amidine derivative (9) by reacting the amide (8) with an alcohol such as ethanol containing a hydrogen halide such as hydrogen chloride and then reacting the reaction product with an ammonium salt such as ammonium carbonate. Benzamidine derivatives (1—1) can be produced by reacting the amidine derivative (9) in the presence of a catalyst such as palladium carbon in an alcohol such as methanol as the solvent in hydrogen atmosphere and then hydrolyzing the reaction product with an acidic aqueous solution such as concentrated hydrochloric acid.

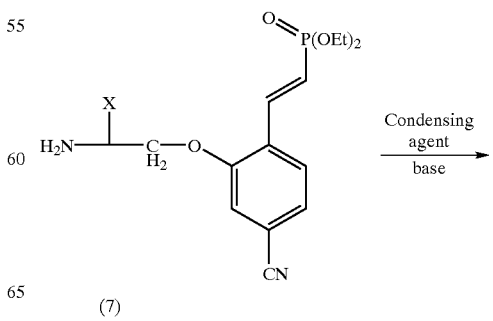

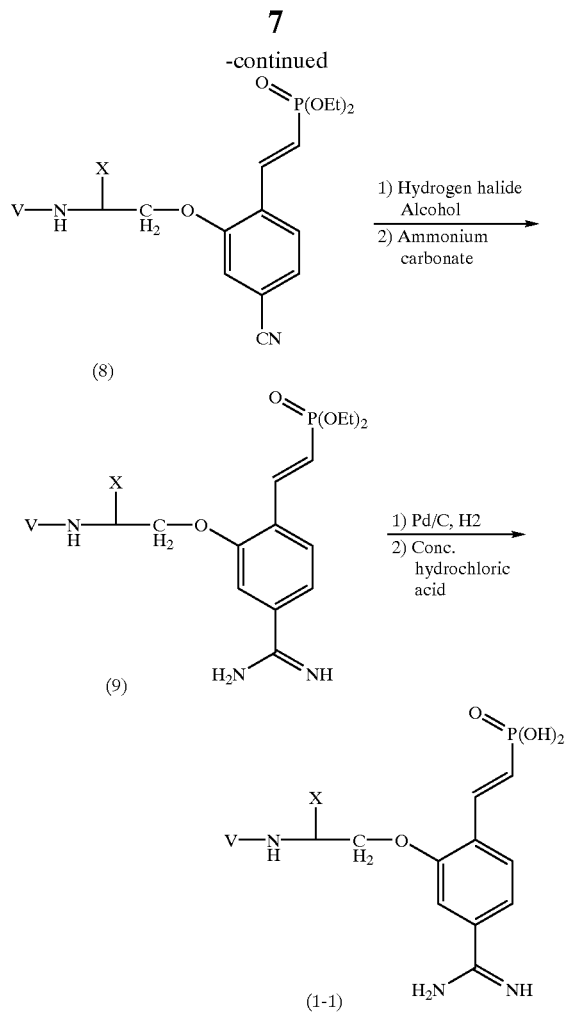

The compounds of general formulae (1) to (2-6) produced as described above and salts thereof can be isolated by the purification by a well-known separation/purification method such as extraction, concentration, concentration under reduced pressure, extraction with a solvent, crystallization, recrystallization, redissolution or various chromatographic techniques.

Optical isomers of benzamidine derivatives represented by general formula (1) of the present invention are possible because they may contain an asymmetric carbon The compounds of the present invention also include mixtures of those optical isomers and isolated compounds.

The amidino group in the compounds of the present invention may be replaced with a suitable substituent which can be changed into the amidino group in vivo. For example, hydrogen atom bonded to nitrogen atom having double bond in amidino group bonded to the benzene ring in general formula (1) is replaced with hydroxyl group, an alkoxyl group such as ethoxyl group, amino group, carboxyl group, an alkoxycarbonyl group such as ethoxycarbonyl group, an alkylsulfonyl group such as ethylsulfonyl group, carbamoyl group, a carbamoyl group in which one or two hydrogen atoms are replaced with an alkyl group such as diethoxycarbamoyl group, formyl group, an acyl group such as acetyl group or an alkylcarboxyl group such as acetoxyl group. The compounds of the present invention having such a substituent are those of formulae (2-5) and (2-6).

The salts of the benzamidine derivatives of general formula (1) to formula (2-6) of the present invention are pharmaceutically acceptable ones such as salts of them with mineral acids, e. g. hydrochloric acid, hydrobromic acid, sulfuric acid, nitric acid and phosphoric acid; and organic acids, e. g. formic acid, acetic acid, trifluoroacetic acid, lactic acid, salicylic acid, mandelic acid, citric acid, oxalic acid, maleic acid, fumaric acid, tartaric acid, tannic acid, malic acid, toluenesulfonic acid, methanesulfonic acid and benzenesulfonic acid.

The compounds of general formula (1) to formula (2-6) and salts thereof of the present invention are administered as they are or in the form of various pharmaceutical compositions to patients. The dosage forms of the pharmaceutical compositions are, for example, tablets, powders, pills, granules, capsules, suppositories, solutions, sugar-coated tablets and depots. They can be prepared with ordinary preparation assistants by an ordinary method. For example, the tablets are prepared by mixing the benzamidine derivative, the active ingredient of the present invention, with known adjuvants such as inert diluents, e. g. lactose, calcium carbonate and calcium phosphate, binders, e. g. acacia, corn starch and gelatin, extending agents, e. g. alginic acid, corn starch and pre-gelatinized starch, sweetening agents, e. g. sucrose, lactose and saccharin, corrigents, e. g. peppermint and cherry, and lubricants, e. g. magnesium stearate, talc and carboxymethyl cellulose.

When the benzamidine derivatives represented by general formula (1) to formula (2-6) are used as the anticoagulants, they can be administered either orally or parenterally. The dose which varies depending on the age, body weight and conditions of the patient and the administration method is usually 0.01 to 1,000 mg, preferably 0.1 to 50 mg, a day for adults in the oral administration, and 1 $\mu$g to 100 mg, preferably 0.01 to 10 mg, in the parenteral administration.

The blood-coagulation inhibitor or the agent for preventing or treating diseases caused by thrombi or emboli, containing one of the compounds of general formula (1) to formula (2-6) and salts thereof is usable for preventing or treating diseases caused by thrombi or emboli, for example, cerebrovascular disorders such as cerebral infarction, cerebral stroke, cerebral thrombosis, cerebral embolism, transient ischemic attack (TIA) and subarachnoidal hemorrhage (vasospasm); ischemic heart diseases such as acute and chronic myocardial infarction, unstable angina and coronary thrombolysis; pulmonary vascular disorders such as pulmonary infarction and pulmonary embolism; peripheral occlusion; deep vein thrombosis; disseminated intravascular coagulation; thrombus formation after an artificial blood vessel-forming operation or artificial valve substitution; re-occlusion and re-stenosis after a coronary bypass-forming operation; re-occlusion and re-stenosis after reconstructive operation for the blood circulation such as percutaneous transluminal coronary angioplasty (PTCA) or percutaneous transluminal coronary recanalization (PTCR); and thrombus formation in the course of the extracorporeal circulation.

The following Examples will further illustrate the present invention, which are only preferred embodiments of the invention and which by no means limit the invention.

EXAMPLE 1

[2-(4-Amidino-2-[2-[(1-(1-pyridine-4-yl)piperidine-4-carbonyl)amino]ethoxy]phenyl)ethyl]phosphoric acid bistrifluoroacetate

Step 1: Synthesis of ethyl 1-(4-pyridyl)-4-piperidinecarboxylate 4.0 g (26.6 mmol) of 4-chloropyridine hydrochloride, 4.2 g (26.6 mmol) of ethyl piperidine-4-carboxylate and 7.4 ml (53.2 mmol) of triethylamine were stirred in 100 ml of xylene at 130° C. for 24 hours. The reaction mixture was treated with dichloromethane as extracting solvent by an ordinary method to obtain the crude compound, which was purified by the silica gel column chromatography to obtain the title compound.

Yield: 2.95 g (12.6 mmol) (47%) H-NMR (CDCl3) δ 1.25 (3H, t), 1.71–1.85 (2H, m), 2.00 (2H, d), 2.50–2.60 (1H, m), 2.90 (2H, t), 3.81 (2H, d), 4.20 (2H, q), 6.66 (2H, d), 8.26 (2H, d).

Step 2: Synthesis of 1-(4-pyridyl)-4-piperidinecarboxylic acid hydrochloride 2.95 g (12.6 mmol) of ethyl 1-(4-pyridyl)-4-piperidinecarboxylate was stirred in 100 ml of dioxane. 50 ml of 1 N hydrochloric acid was added to the obtained mixture, and they were stirred at 95° C. for 20 hours. The solvent was evaporated to obtain the crude title compound.

Yield: 3.21 g (11.5 mmol) (91%) H-NMR (DMSO-d6) δ 1.54 (2H, t), 1.90 (2H, t), 2.60–2.70 (1H, m), 3.30 (2H, t), 4.10 (2H, d), 7.19 (2H, d), 8.20 (2H, d).

Step 3 Synthesis of 3-hydroxy-4-iodobenzoic acid 30.0 g (217 mmol) of 3-hydroxybenzoic acid was dissolved in 200 ml of acetic acid. 53.0 g (326 mmol) of iodine monochloride was added to the obtained solution at room temperature. After stirring at 45° C. for 15 hours, the solvent was evaporated under reduced pressure. The residue was washed with 500 ml of 1% aqueous sodium thiosulfate solution twice and with 500 ml of water twice and then dried to solid at 80° C. under reduced pressure to obtain the title compound.

Yield: 17.2 g (65.2 mmol) (yield: 30%) MS (FAB, m/z) 265 (MH+) H-NMR (DMSO-d6) δ 7.13 (1H, dd), 7.43 (1H, d), 7.80 (1H, d).

Step 4: Synthesis of 3-hydroxy-4-iodobenzonitrile 22.3 g (89.7 mmol) of 3-hydroxy-4-iodobenzoic acid was dissolved in 300 ml of tetrahydrofuran. 19.7 ml (206 mmol) of ethyl chloroformate and 28.7 ml (206 mmol) of triethylamine were added to the obtained solution at 0° C. After stirring for 15 minutes, triethylamine hydrochloride thus formed was filtered out. The filtrate was added to 300 ml of a tetrahydrofuran solution, obtained by bubbling ammonia, at 0° C. After stirring at room temperature for 10 hours, the solvent was evaporated under reduced pressure. The residue thus obtained was dissolved in 450 ml of dioxane. 17.4 ml (117 mmol) of anhydrous trifluoromethanesulfonic acid and 21.8 ml (269 mmol) of pyridine were added to the obtained solution at 0° C. After stirring at room temperature for 18 hours, the solvent was evaporated under reduced pressure. The residue was treated with chloroform as the extracting solvent by an ordinary method to obtain an oily residue. The residue was dissolved in 180 ml of tetrahydrofuran/methanol (1/1). 90 ml (90.0 mmol) of 1 N aqueous sodium hydroxide solution was added to the obtained solution at room temperature. The mixture was stirred for 4 hours. The solvent was evaporated under reduced pressure. The residue was washed with dichloromethane, then acidified with 1 N hydrogen chloride and treated with ethyl acetate as the extracting solvent by an ordinary method to obtain the crude product. The crude product was purified by the silica gel column chromatography to obtain the title compound.

Yield: 9.29 g (37.9 mmol) (42%) MS (FAB, m/z) 246 (MH+) H-NMR (CDCl3) δ 5.63 (1H, br), 6.96 (1H, dd), 7.23 (1H, d), 7.79 (1H, d)

Step 5: Synthesis of t-butyl (2-bromoethyl) carbamate 9.22 g (45 mmol) of 2-bromoethylamine hydrobromide was dissolved in 100 ml of dichloromethane. 7.64 g (35 mmol) of di-t-butyl dicarbonate, 10.0 g (99 mmol) of triethylamine and 100 mg (0.82 mmol) of 4-(dimethylamino)pyridine were added to the obtained solution, and they were stirred overnight. After the treatment with dichloromethane as the extracting solvent by an ordinary method, the title compound was obtained.

Yield: 5.99 g (26.7 mmol) (76%) H-NMR (CDCl3) δ 1.45 (9H, s), 3.46 (2H, dt), 3.51 (2H, t), 4.95 (1H, br)

Step 6 Synthesis of 3-[2-(t-butoxycarbonylamino) ethoxy]-4-iodobenzonitrile 18.5 g (82.6 mmol) of t-butyl (2-bromoethyl)carbamate was dissolved in 200 ml of DMF. 10.1 g (41.3 mmol) of 3-hydroxy-4-iodobenzonitrile and 5.7 g (41.3 mmol) of potassium carbonate were added to the obtained solution, and they were stirred at 75° C. for 3 hours. After the treatment with ethyl acetate as the extracting solvent by an ordinary method, the title compound was obtained.

Yield: 11.0 g (28.4 mmol) (69%) H-NMR (CDCl3) δ 1.46 (9H, s), 3.62 (2H, dt), 4.12 (2H, t), 7.02 (2H, d), 7.88 (2H, d).

Step 7 Synthesis of methyl 2-(2-(t-butoxycarbonylamino)ethoxy)-4-cyanobenzoate 5 g (12.88 mmol) of 3-(2-(t-butoxycarbonylamino) ethoxy)-4-iodobenzonitrile was dissolved in 60 ml of N,N-dimethylformamide (dehydrated). 3.6 ml (25.8 mmol) of triethylamine, 10 ml (25.8 mmol) of methanol and 145 mg (0.644 mmol) of palladium acetate were added to the obtained solution, and they were stirred in the presence of carbon monoxide at 90° C. for 6 hours. The solvent was evaporated, and the residue was treated with ethyl acetate as the extracting solvent by an ordinary method to obtain the crude product, which was purified by the silica gel column chromatography to obtain the title compound.

Yield: 4.11 g (12.82 mmol) (99.5%) H-NMR (CDCl3) δ 1.44 (9H, s), 3.61 (2H, q), 3.94 (3H, s), 4.12 (2H, m), 5.38 (1H, br), 7.21 (1H, s), 7.38 (1H, m), 7.87 (1H, d).

Step 8 Synthesis of 3-(2-(t-butoxycarbonylamino) ethoxy)-4-hydroxymethylbenzonitrile 4.15 g (12.95 mmol) of methyl 2-(2-(t-butoxycarbonylamino)ethoxy)-4-cyano-benzoate was dissolved in 60 ml of tetrahydrofuran (dehydrated). 8.6 ml (17.2 mmol) of 2 M lithium borohydride was added to the obtained solution under cooling with ice, and they were stirred at room temperature overnight. The solvent was evaporated, and the residue was treated with ethyl acetate as the extracting solvent by an ordinary method to obtain the crude product, which was purified by the silica gel column chromatography to obtain the title compound.

Yield: 2.38 g (8.12 mmol) (63%) H-NMR (CDCl3) δ 1.41 (9H, s), 3.00 (1H, br), 3.60 (2H, br), 4.10 (2H, t), 4.70 (2H, d), 4.95 (1H, br), 7.07 (1H, s), 7.30 (1H, d), 7.41 (1H, d).

Step 9 Synthesis of 3-(2-(t-butoxycarbonylamino) ethoxy)-4-formylbenzonitrile 0.3 g (1.03 mmol) of 3-(2-(t-butoxycarbonylamino) ethoxy)-4-hydroxymethylbenzonitrile was dissolved in 3 ml of dichloromethane (dehydrated). 0.36 g (4.1 mmol) of activated manganese dioxide was added to the obtained solution in the presence of argon, and they were stirred at room temperature overnight. The reaction solution was filtered through Celite to obtain the title compound.

Yield: 279 mg (0.962 mmol) (93%) MS (ESI, m/z) 291 (MH−) H-NMR (CDCl3) δ 1.53 (9H, s), 3.62 (2H, q), 4.20 (2H, t), 4.95 (1H, br), 7.35 (2H, m), 7.93 (1H, d), 10.50 (1H, s).

Step 10: Synthesis of diethyl [2-[(2-(2-t-butoxycarbonylamino)ethoxy)-4-cyano-phenyl]vinyl]phosphate 0.54 ml (2.18 mmol) of tetraethylmethylene diphosphonate was dissolved in 10 ml of tetrahydrofuran (dehydrated). 1.5 ml (1.0 mmol) of 1.54 M solution of n-butyllithium in hexane was added to the obtained solution in the presence of argon at −78° C., and they were stirred for 20 minutes. 527 mg (1.82 mmol) of 3-(2-(t-butoxycarbonylamino)ethoxy)-4-formylbenzonitrile was added to the reaction mixture, and they were stirred at −78° C. for 45 minutes and then at room temperature for 3 hours. The solvent was evaporated, and the residue was treated with dichloromethane as the extracting solvent by an ordinary method to obtain the crude product, which was purified by the silica gel column chromatography to obtain the title compound.

Yield: 0.45 g (1.06 mmol) (58%) H-NMR (CDCl3) δ 1.17–1.42 (6H, m), 1.47 (9H, s), 3.60 (2H, br), 3.96–4.23 (6H, m), 5.00 (1H, br), 6.40 (2H, m), 7.15 (1H, s), 7.27 (1H, d), 7.58 (1H, d).

Step 11: Synthesis of diethyl [2-(4-amidino-2-[2-[(1-(1-pyridine-4-yl)piperidine-4-carbonyl)amino]ethoxy]phenyl)vinyl]phosphate bistrifluoroacetate Synthesis of monoethyl [2-(4-amidino-2-[2-[(1-(1-pyridine-4-yl)piperidine-4-carbonyl)amino]ethoxy]phenyl)vinyl]phosphate bistrifluoroacetate:

0.45 g (1.06 mmol) of diethyl [2-[(2-(2-t-butoxycarbonylamino)ethoxy)-4-cyano-phenyl]vinyl]phosphate was dissolved in a mixture of 5 ml of dioxane and 5 ml of 4 N solution of hydrogen chloride in dioxane, and the obtained solution was stirred at room temperature for 3 hours. The solvent was evaporated, and the obtained crude product was dissolved in 10 ml of N,N-dimethylformamide (dehydrated). 0.29 g (1.2 mmol) of 1-(4-pyridyl)-4-piperidinecarboxylic acid hydrochloride, 0.5 g (2.8 mmol) of 2-chloro-1,3-dimethylimidazonium chloride and 1.8 ml (12.8 mmol) of triethylamine were added to the obtained solution, and they were stirred overnight. The reaction mixture was treated with dichloromethane as the extracting solvent by an ordinary method to obtain the crude product, which was dissolved in a mixture of 5 ml of 4 N solution of hydrogen chloride in dioxane and 0.5 ml of ethanol, and the obtained solution was stirred at room temperature for 3 days. The solvent was evaporated, and the obtained residue was dissolved in 5 ml of ethanol. 0.19 g (3.35 mmol) of ammonium carbonate was added to the obtained solution, and they were stirred at room temperature overnight. The solvent was evaporated, and the obtained crude product was treated by the reversed phase high-performance liquid chromatography with column of silica gel of chemically bonded with octadodecyl group as the filler and eluted with a solvent mixture of water and acetonitrile containing 0.1% (V/V) of trifluoroacetic acid. The intended fraction was freeze-dried to obtain the title compound. Diethyl [2-(4-amidino-2-[2-[(1-(1-pyridine-4-yl)piperidine-4-carbonyl)amino]ethoxy]phenyl)vinyl]phosphate bistrifluoroacetate:

Yield: 155 mg (0.204 mmol) (31%) MS (ESI, m/z) 530 (MH+) H-NMR (DMSO-d6) δ 1.26 (6H, t), 1.50–1.92 (4H, m), 2.58 (2H, br), 3.22 (2H, t), 3.50 (2H, br), 4.03 (4H, m), 4.20 (3H, br), 6.77 (2H, m), 7.19 (2H, d), 7.40–7.74 (3H, m), 7.96 (1H, d), 8.21 (2H, d), 9.33(2H, br), 9.36 (2H, br).

Synthesis of monoethyl [2-(4-amidino-2-[2-[(1-(1-pyridine-4-yl)piperidine-4-carbonyl)amino]ethoxy]phenyl)vinyl]phosphate bistrifluoroacetate:

Yield: 63.4 mg (0.087 mmol) (13%) MS (ESI, m/z) 502 (MH+) H-NMR (DMSO-d6) δ 1.23 (3H, t), 1.50–1.95 (4H, m), 2.58 (2H, br), 3.22 (2H, t), 3.50 (2H, br), 3.95 (2H, m), 4.22 (3H, br), 6.71 (2H, m), 7.18 (2H, d), 7.38–7.66 (3H, m), 7.92 (1H, d), 8.20 (2H, d), 9.21(2H, br), 9.34 (2H, br).

Step 12: Synthesis of monoethyl [2-(4-amidino-2-[2-[(1-(1-pyridine-4-yl)piperidine-4-carbonyl)amino]ethoxy]phenyl)ethyl]phosphate bistrifluoroacetate 63.4 mg (0.087 mmol) of monoethyl[2-(4-amidino-2-[2-[(1-(1-pyridine-4-yl)piperidine-4-carbonyl9amino]ethoxy)phenyl]vinyl]-phosphate bistrifluoroacetate was dissolved in 2 ml of ethanol. 10 mg of 10% palladium/carbon (50% hydrous) was added to the obtained solution in argon atmosphere, and they were stirred in the presence of hydrogen at room temperature overnight. 2 ml of water was added to the reaction mixture. The solvent was evaporated, and the obtained crude product was treated in the same manner as that in Step 11 in Example 1 to obtain the title compound.

Yield: 43.1 mg (0.059 mmol) (68%) MS (ESI, m/z) 504 (MH+) H-NMR (DMSO-d6) δ 1.20 (3H, t), 1.58 (2H, br), 1.80–1.96 (4H, m), 2.62 (2H, br), 2.80 (2H, br), 3.21 (2H, t), 3.49 (2H, q), 3.88–3.98 (2H, m), 4.12 (2H, t), 4.20 (1H, br), 7.18 (2H, d), 7.37–7.42 (3H, m), 8.21 (2H, 8.28 (1H, br), 9.18(2H, br), 9.25 (2H, br).

Step 13 Synthesis of [2-(4-amidino-2-[2-[(1-(1-pyridine-4-yl)piperidine-4-carbonyl)amino]ethoxy]phenyl)ethyl]phosphoric acid bistrifluoroacetate 27.5 mg (37.59 mmol) of monoethyl[2-(4-amidino-2-[2-[(1-(1-pyridine-4-yl)piperidine-4-carbonyl)amino]ethoxy]phenyl)ethyl]-phosphate bistrifluoroacetate was dissolved in 2 ml of concentrated hydrochloric acid, and the obtained solution was stirred at 80° C. for 11 hours. The solvent was evaporated, and the obtained crude product was treated in the same manner as that in Step 11 in Example 1 to obtain the title compound.

Yield: 9 mg (12.79 mmol) (34%) MS (ESI, m/z) (MH+) 476 H-NMR (DMSO-d6) δ 1.50–2.20 (6H, m), 2.69 (2H, br), 2.83 (2H, br), 3.14–3.36 (2H, m), 3.49 (2H, br), 4.07–4.26 (3H, m), 7.14–7.24 (3H, m), 7.32–7.44 (2H, m), 8.21 (2H, d), 8.34 (1H, br), 9.23 (3H, br).

EXAMPLE 2

[2-(4-amidino-2-[2-[4-(1-(1-acetimidoyl)-4-piperidyloxy)benzoylamino]ethoxy]phenyl)ethyl] phosphoric acid bistrifluoroacetate Step 1 Synthesis of diethyl [2-[(2-(2-t-butoxycarbonylamino)ethoxy)-4-cyano-phenyl]vinyl]phosphate 10 g (25.76 mmol) of 3-(2-(t-butoxycarbonylamino)ethoxy)-4-iodobenzonitrile was dissolved in 100 ml of N,N-dimethylformamide (dehydrated). 4.75 ml (30.91 mmol) of diethylvinyl phosphonate, 58 mg (0.258 mmol) of palladium acetate and 160 mg (0.515 mmol) of tris(2-methylphenyl)phosphine were added to the obtained solution, and they were stirred at 100° C. overnight. The solvent was evaporated, and the obtained product was treated with ethyl acetate as the extracting solvent by an ordinary method to obtain the crude product, which was purified by the silica gel column chromatography to obtain the title compound.

Yield: 9.46 g (22.3 mmol) (87%) H-NMR (CDCl3) δ 1.38 (6H, t), 2.15 (2H, br), 3.60 (2H, br), 4.11 (4H, m), 5.18 (1H, br), 6.40 (1H, t), 7.13 (1H, s), 7.29 (1H, m), 7.58 (1H, d), 7.72–7.86 (1H, m).

Step 2 Synthesis of diethyl [2-(4-amidino-2-[2-[4-(4-piperidyloxy)benzoylamino]ethoxy]phenyl)vinyl] phosphate bistrifluoroacetate 1.5 g (3.53 mmol) of diethyl [2-[(2-(2-t-butoxycarbonylamino)ethoxy)-4-cyano-phenyl]vinyl] phosphate was dissolved in a mixture of 15 ml of dioxane and 15 ml of 4 N solution of hydrogen chloride in dioxane, and they were stirred at room temperature for 2 hours. The solvent was evaporated, and the obtained crude product was dissolved in 10 ml of N,N-dimethylformamide (dehydrated). 1.25 g (3.88 mmol) of 4-(1-t-butoxycarbonyl-4-piperidyloxy)benzoic acid, 0.78 g (4.59 mmol) of 2-chloro-1,3-dimethylimidazonium chloride and 3 ml (21.2 mmol) of triethylamine were added to the obtained solution, and they were stirred for 4 hours. The solvent was evaporated, and the obtained crude product was dissolved in 50 ml of 4 N solution of hydrogen chloride in dioxane. 5 ml of ethanol was added to the obtained solution, and they were stirred at room temperature overnight. The solvent was evaporated, and the residue was dissolved in 10 ml of ethanol. 1 g (17.65 mmol) of ammonium carbonate was added to the obtained solution, and they were stirred at room temperature overnight. The solvent was evaporated, and the obtained crude product was dissolved in a mixture of 30 ml of dioxane and 30 ml of 4 N solution of hydrogen chloride in dioxane, and the obtained solution was stirred at room temperature for 2 hours. The solvent was evaporated, and the obtained crude product was treated in the same manner as that in step 11 in Example 1 to obtain the title compound.

Yield: 1.45 g (1.88 mmol) (53%)

Step 3 Synthesis of diethyl [2-(4-amidino-2-[2-[4-(1-(1-acetimidoyl)-4-piperidyloxy)benzoylamino] ethoxy]phenyl)ethyl]phosphate bistrifluoroacetate 1.45 g (1.88 mmol) of diethyl [2-(4-amidino-2-[2-[4-(4-piperidyloxy)benzoylamino]ethoxy]phenyl)vinyl]phosphate bistrifluoroacetate obtained in step 2 was dissolved in 50 ml of ethanol. 0.695 g (5.65 mmol) of ethyl acetimidate hydrochloride and 1.31 ml (9.38 mmol) of triethylamine were added to the obtained solution, and they were stirred overnight. The solvent was evaporated, and the obtained crude product was dissolved in 50 ml of ethanol. 150 mg of 10% palladium/carbon was added to the obtained solution, and they were stirred in the presence of hydrogen overnight. After the filtration through Celite, the solvent was evaporated. The obtained crude product was treated in the same manner as that in step 11 in Example 1 to obtain the title compound.

Yield: 98 mg (0.12 mmol) (6%) MS (ESI, m/z) 588 (MH+) H-NMR (DMSO-d6) δ 1.17 (6H, t), 1.80 (2H, br), 1.95–2.20 (4H, m), 2.30 (3H, s), 2.85 (2H, br), 3.40–3.80 (6H, m), 3.90 (4H, q), 4.25 (2H, br), 4.80 (1H, br), 7.06 (2H, d), 7.42 (3H, m), 7.86 (2H, d), 8.60 (2H, br), 9.11 (3H, br), 9.26 (2H, br).

Step 4 Synthesis of monoethyl [2-(4-amidino-2-[2-[4-(4-piperidyloxy)benzoylamino]ethoxy]phenyl) ethyl]phosphate bistri-fluoroacetate Synthesis of [2-(4-amidino-2-[2-[4-(4-piperidyloxy) benzoylamino]ethoxy]phenyl)ethyl]phosphate bistri-fluoroacetate:

0.3 g (0.478 mmol) of diethyl [2-(4-cyano-2-[2-[4-(1-(1-t-butoxycarbonyl)-4-piperidyloxy)benzoylamino]ethoxy] phenyl)vinyl]phosphate obtained in the same manner as that in step 2 was dissolved in 30 ml of ethanol. 30 mg of 10% palladium/carbon was added to the obtained solution, and they were stirred in the presence of hydrogen overnight. After the filtration through Celite, the solvent was evaporated. The obtained crude product was dissolved in a mixture of 10 ml of dioxane and 10 ml of 4 N solution of hydrogen chloride in dioxane, and the obtained solution was stirred at room temperature for 1 hour. The solvent was evaporated, and the obtained crude product was dissolved in 30 ml of 4 N solution of hydrogen chloride in dioxane. 3 ml of ethanol was added to the obtained solution, and they were stirred at room temperature overnight. The solvent was evaporated, and the residue was dissolved in 10 ml of ethanol. 0.2 g (3.5 mmol) of ammonium carbonate was added to the obtained solution, and they were stirred at room temperature overnight. The solvent was evaporated, and the obtained crude product was dissolved in 5 ml of concentrated hydrochloric acid. The obtained solution was stirred at 80° C. for 4 hours. The solvent was evaporated, and the obtained crude product was treated in the same manner as that in step 11 in Example 1 to obtain the title compound.

Monoethyl[2-(4-amidino-2-[2-[4-(4-piperidyloxy) benzoylamino]ethoxy]phenyl)ethyl]phosphate bistrifluoroacetate:

Yield: 53.2 mg (0.07 mmol) (15%) MS (ESI, m/z) 519 (MH+) H-NMR (DMSO-d6) δ 1.16 (3H, t), 1.75–2.00 (4H, m), 2.10 (2H, br), 2.85 (2H, br), 3.10 (2H, br), 3.25 (2H, br), 3.60–4.00 (4H, m), 4.20 (2H, br), 4.75 (1H, br), 7.05 (2H, d), 7.41 (3H, m), 7.86 (2H, d), 8.60 (2H, m), 9.10 (2H, br), 9.25 (2H, br).

[2-(4-Amidino-2-[2-[4-(4-piperidyloxy)benzoylamino] ethoxy]phenyl)-ethyl]phosphoric acid:

Yield: 6.96 mg (0.0096 mmol) (2%) MS (ESI, m/z) 491 (MH+) H-NMR (DMSO-d6) δ 1.80 (4H, br), 2.10 (2H, br), 2.95 (2H, br), 3.00–3.75 (6H, m), 4.20 (2H, br), 4.70 (1H, br), 7.05 (2H, d), 7.40 (3H, m), 7.88 (2H, d), 8.56 (1H, br), 8.74 (1H, br), 9.06 (2H, br), 9.22 (2H, br).

Step 5 Synthesis of monoethyl [2-(4-amidino-2-[2-[4-(1-(1-acetimidoyl)-4-piperidyloxy)benzoylamino] ethoxy]phenyl)ethyl]phosphate bistrifluoroacetate 46.94 mg (0.063 mmol) of monoethyl [2-(4-amidino-2-[2-[4-(4-piperidyloxy)benzoylamino]ethoxy]phenyl)ethyl] phosphate bistrifluoroacetate obtained in step 4 was dissolved in 5 ml of ethanol. 75 mg (0.57 mmol) of ethyl acetimidate hydrochloride and 0.15 ml (0.945 mmol) of triethylamine were added to the obtained solution, and they were stirred overnight. The solvent was evaporated, and the obtained crude product was treated in the same manner as that in step 11 in Example 1 to obtain the title compound.

Yield: 34.26 mg (mmol) (69%) MS (ESI, m/z) 560 (MH+) H-NMR (DMSO-d6) δ 1.16 (3H, t), 1.70–2.00 (4H, m), 2.10 (2H, br), 2.30 (3H, s), 2.85 (2H, m), 3.50 (2H, m), 3.60–3.80 (4H, m), 3.88 (2H, q), 4.20 (2H, br), 4.80 (1H, br), 7.06 (2H, d), 7.41 (3H, m), 7.86 (2H, d), 8.60 (1H, br), 8.66 (1H, br), 9.13 (3H, br), 9.24 (2H, br).

Step 6 Synthesis of [2-(4-amidino-2-[2-[4-(1-(1-acetimidoyl)-4-piperidyloxy)benzoylamino]ethoxy] phenyl)ethyl]phosphate bistrifluoroacetate 6.96 mg (0.0096 mmol) of [2-(4-amidino-2-[2-[4-(4-piperidyloxy)benzoylamino]ethoxy]phenyl)ethyl] phosphoric acid bistrifluoroacetate obtained in step 4 was dissolved in 5 ml of ethanol. 14 mg (0.086 mmol) of ethyl acetimidate hydrochloride and 0.03 ml (0.144 mmol) of triethylamine were added to the obtained solution, and they were stirred overnight. The solvent was evaporated, and the same procedure as that in step 11 in Example 1 was repeated to obtain the title compound.

Yield: 4.87 mg (0.0064 mmol) (67%) MS (ESI, m/z) 532 (MH+) H-NMR (DMSO-d6) δ 1.70–1.90 (4H, m), 2.10 (2H, br), 2.30 (3H, s), 2.85 (2H, br), 2.65 (2H, br), 3.60–3.85 (4H, m), 4.20 (2H, br), 4.80 (1H, br), 7.06 (2H, d), 7.40 (3H, m), 7.87 (2H, d), 8.60 (1H, br), 8.72 (1H, br), 9.08 (2H, br), 9.16 (1H, br), 9.22 (2H, br).

EXAMPLE 3

[2-(4-Amidino-2-[2-[4-(1-pyrrolidinecarbamoyl) benzoylamino]ethoxy]phenyl)ethyl]phosphoric acid mono-trifluoroacetate Step 1: Synthesis of diethyl [2-(4-cyano-2-[2-[4-(1-pyrrolidinecarbamoyl)benzoylamino]ethoxy]phenyl) vinyl]phosphate 0.57 g (1.34 mmol) of diethyl [2-[(2-(2-t-butoxycarbonylamino)ethoxy)-4-cyano-phenyl]vinyl] phosphate was dissolved in a mixture of 10 ml of dioxane and 10 ml of 4 N solution of hydrogen chloride in dioxane, and the obtained solution was stirred at room temperature for 1.5 hours. The solvent was evaporated, and the obtained crude product was dissolved in 20 ml of N,N-dimethylformamide (dehydrated). 0.32 g (1.47 mmol) of pyrrolidylcarbamoylbenzoic acid, 0.32 g (1.74 mmol) of 2-chloro-1,3-dimethylimidazonium chloride and 1.2 ml (8.04 mmol) of triethylamine were added to the obtained solution, and they were stirred overnight. The solvent was evaporated, and the obtained crude product was treated in the same manner as that in step 11 in Example 1 to obtain the title compound.

Yield: 0.52 g (0.99 mmol) (74%) MS (ESI, m/z) 526 (MH+) H-NMR (CDCl3) δ 1.34 (6H, t), 1.80–2.05 (4H, m), 3.40 (2H, t), 3.60 (2H, t), 3.95 (2H, br), 4.13 (4H, q), 4.25 (2H, t), 6.40 (2H, m), 7.17 (1H, s), 7.54 (2H, d), 7.63 (1H, d), 7.85 (2H, d), 8.20 (1H, d).

Step 2 Synthesis of diethyl [2-(4-amidino-2-[2-[4-(1-pyrrolidinecarbamoyl)benzoylamino]ethoxy] phenyl)ethyl]phosphate mono-trifluoroacetate 0.5 g (0.95 mmol) of diethyl [2-(4-cyano-2-[2-[4-(1-pyrrolidinecarbamoyl)benzoylamino]ethoxy]phenyl)vinyl] phosphate obtained in step 1 was dissolved in 10 ml of 4 N solution of hydrogen chloride in dioxane. 1 ml of ethanol was added to the obtained solution, and they were stirred at room temperature overnight. The solvent was evaporated, and the obtained residue was dissolved in 5 ml of ethanol. 0.3 g (4.76 mmol) of ammonium carbonate was added to the obtained solution, and they were stirred at room temperature overnight. The solvent was evaporated, and the residue was dissolved in 5 ml of ethanol. 0.1 g of 10% palladium/carbon was added to the obtained solution, and they were stirred in the presence of hydrogen at room temperature overnight. After the filtration through Celite, the solvent was evaporated, and the obtained crude product was treated in the same manner as that in step 11 in Example 1 to obtain the title compound.

Yield: 306 mg (0.46 mmol) (49%) MS (ESI, m/z) 545 (MH+) H-NMR (DMSO-d6) δ 1.16 (6H, t), 1.75–2.10 (6H, m), 2.83 (2H, br), 3.35 (2H, t), 3.45 (2H, t), 3.70–4.00 (6H, m), 4.30 (2H, br), 7.42 (2H, m), 7.58 (3H, m), 7.90 (2H, d), 8.86 (1H, br), 9.02 (2H, br), 9.25 (2H, br).

Step 3 Synthesis of monoethyl [2-(4-amidino-2-[2-[4-(1-pyrrolidinecarbamoyl)benzoylamino]ethoxy] phenyl)ethyl]phosphate mono-trifluoroacetate Synthesis of [2-(4-amidino-2-[2-[4-(1-pyrrolidinecarbamoyl)benzoylamino]ethoxy]phenyl)ethyl] phosphoric acid mono-trifluoroacetate:

268 mg (0.41 mmol) of diethyl [2-(4-amidino-2-[2-[4-(1-pyrrolidinecarbamoyl)benzoylamino]ethoxy]phenyl)ethyl] phosphate mono-trifluoroacetate obtained in step 2 was dissolved in 3 ml of concentrated hydrochloric acid, and the obtained solution was stirred at 80° C. for 8 hours. The solvent was evaporated, and the obtained crude product was treated in the same manner as that in step 11 in Example 1 to obtain the title compound.
Monoethyl[2-(4-amidino-2-[2-[4-(1-pyrrolidinecarbamoyl) benzoylamino]ethoxy]phenyl)ethyl]phosphate mono-trifluoroacetate:

Yield: 14.07 mg (0.022 mmol) (5%) MS (ESI, m/z) 517 (MH+) H-NMR (DMSO-d6) δ 1.16 (3H, t), 1.78–2.00 (6H, m), 2.85 (2H, br), 3.34 (2H, br), 3.47 (2H, br), 3.72 (2H, br), 3.90 (2H, m), 4.30 (2H, br), 7.41 (3H, m), 7.58 (2H, d), 7.91 (2H, d), 8.90 (1H, br), 9.01 (2H, br), 9.22 (2H, br).
[2-(4-Amidino-2-[2-[4-(1-pyrrolidinecarbamoyl) benzoylamino]ethoxy]-phenyl)ethyl]phosphoric acid mono-trifluoroacetate:

Yield: 7.8 mg (0.013 mmol) (3%) MS (ESI, m/z) 489 (MH+) H-NMR (DMSO-d6) δ 1.75–1.92 (6H, m), 2.85 (2H, br), 3.35 (2H, br), 3.50 (2H, br), 3.70 (2H, br), 4.25 (2H, br), 7.40 (3H, m), 7.59 (2H, d), 7.91 (2H, d), 8.94 (1H, br), 9.00 (2H, br), 9.23 (2H, br).

EXAMPLE 4

(4S)-5-(5-Amidino-2-(2-(diethoxyphosphoryl)ethyl) phenoxy)-4-((1-(1-pyridine-4-yl)piperidine-4-carbonyl)-amino)pentanoic acid bistrifluoroacetate Step 1 Synthesis of benzyl (4S)-4-((t-butoxycarbonyl)amino)-5-hydroxypentanoate 25 g (74.1 mmol) of γ-benzyl t-butoxycarbonyl-D-glutamate was dissolved in 350 ml of tetrahydrofuran. 7.1 ml (74.1 mmol) of ethyl chloroformate and 10.3 ml (74.1 mmol) of triethylamine were added to the obtained solution at 0° C. After stirring for 20 minutes, triethylamine hydrochloride thus formed was filtered out, and 5 g of ice and 2.8 g (74.1 mmol) of sodium borohydride were added to the residue at 0° C., and they were stirred at room temperature for 1 hour. 100 ml of 1 N hydrogen chloride was added to the reaction mixture, and they were stirred for 1 hour. The solvent was evaporated, and the residue was treated with ethyl acetate as the extracting solvent by an ordinary method to obtain the crude product, which was purified by the silica gel column chromatography to obtain the title compound.

Yield: 11.25 g (34.8 mmol) (47%) H-NMR (CDCl3) δ 1.43 (9H, s), 2.50 (2H, br), 3.50–3.70 (4H, m), 4.80 (1H, br), 5.10 (2H, s), 7.35 (5H, s).

Step 2 Synthesis of benzyl (4S)-4-((t-butoxycarbonyl)amino)-5-(3-ethenylphenoxy) pentanoate 11.25 g (34.8 mmol) of benzyl (4S)-4-((t-butoxycarbonyl) amino)-5-hydroxypentanoate acid obtained in step 1 was dissolved in 120 ml of dichloromethane. 9.7 ml (69.6 mmol) of triethylamine was added to the obtained solution. 6.0 ml (52.2 mmol) of mesyl chloride was added to the obtained mixture at 0° C., and they were stirred at room temperature for 4 hours. The solvent was evaporated, and the residue was treated with ethyl acetate as the extracting solvent by an ordinary method to obtain the crude product. This crude product was dissolved in 100 ml of N,N-dimethylformamide (dehydrated). 7.4 g (174 mmol) of lithium chloride was added to the obtained solution, and they were stirred at 50° C. for 6 hours. The solvent was evaporated, and the residue was treated with ethyl acetate as the extracting solvent by an ordinary method to obtain the crude product, which was dissolved in 150 ml of N,N-dimethylformamide (dehydrated). 6.8 g (27.7 mmol) of 3-hydroxy-4-iodobenzonitrile, 5.73 g (41.5 mmol) of potassium carbonate and 4.6 g (27.7 mmol) of potassium iodide were added to the obtained solution, and they were stirred at 90° C. overnight. The solvent was evaporated, and the residue was treated with ethyl acetate as the extracting solvent by an ordinary method to obtain the crude product, which was then purified by the silica gel column chromatography to obtain the title compound.

Yield: 6.64 g (13.5 mmol) (39%) H-NMR (CDCl3) δ 1.44 (9H, s), 2.50 (2H, br), 3.60 (2H, br), 3.93 (2H, br), 4.90 (1H, br), 5.10 (2H, s), 6.94–7.04 (2H, m), 7.36 (5H, s), 7.88 (1H, d).

Step 3: Synthesis of benzyl (4S)-4-((t-butoxycarbonyl)amino)-5-(2-((E)-2-(diethoxyphosphoryl)ethenyl)-5-ethenylphenoxy)pentanoate 2.2 g (4.47 mmol) of benzyl (4S)-4-((t-butoxycarbonyl)amino)-5-(3-ethenylphenoxy)pentanoate obtained in step 2 was dissolved in 20 ml of N,N-dimethylformamide (dehydrated). 0.82 ml (5.36 mmol) of diethylvinyl phosphonate, 11 mg (0.05 mmol) of palladium acetate and 30 mg (0.09 mmol) of tris(2-methylphenyl)phosphine were added to the obtained solution, and they were stirred at 90° C. overnight. The solvent was evaporated, and the obtained residue was treated with ethyl acetate as the extracting solvent by an ordinary method to obtain the crude product, which was then purified by the silica gel column chromatography to obtain the title compound.

Yield: 1.66 g (2.82 mmol) (63%) H-NMR (CDCl3) δ 1.33 (6H, m), 1.43 (9H, s), 2.40–2.60 (2H, m), 3.85–4.20 (8H, m), 5.00 (1H, br), 5.13 (2H, s), 6.00–6.50 (2H, m), 7.10–7.80 (8H, m).

Step 4 Synthesis of (4S)-5-(5-amidino-2-(2-(diethoxyphosphoryl)ethyl)phenoxy)-4-((1-(1-pyridine-4-yl)piperidine-4-carbonyl)-amino)pentanoic acid bistrifluoroacetate Synthesis of (4S)-5-(5-amidino-2-(2-(ethoxy(hydroxy)phosphoryl)ethyl)phenoxy)-4-((1-(1-pyridine-4-yl)piperidine-4-carbonyl)-amino)pentanoic acid bistrifluoroacetate:

0.414 g (0.71 mmol) of benzyl (4S)-4-((t-butoxycarbonyl)amino)-5-(2-((E)-2-(diethoxyphosphoryl)ethenyl)-5-ethenylphenoxy)pentanoate was dissolved in a mixture of 3 ml of dioxane and 3 ml of 4 N solution of hydrogen chloride in dioxane, and the obtained solution was stirred at room temperature for 2 hours. The solvent was evaporated, and the obtained crude product was dissolved in 5 ml of N,N-dimethylformamide (dehydrated). 0.16 g (0.78 mmol) of (1-pyridine-4-yl)piperidine-4-carboxylic acid, 0.15 g (0.92 mmol) of 2-chloro-1,3-dimethylimidazonium chloride and 0.6 ml (4.2 mmol) of triethylamine were added to the obtained solution, and they were stirred at room temperature overnight. The solvent was evaporated, and the obtained crude product was treated in the same manner as that in Step 11 in Example 11. The obtained compound was dissolved in 2.6 ml of 4 N solution of hydrogen chloride in dioxane. 0.26 ml of ethanol was added to the obtained solution, and they were stirred at room temperature overnight. The solvent was evaporated, and the obtained crude product was dissolved in 5 ml of ethanol. 0.2 g (3.53 mmol) of ammonium carbonate was added to the obtained solution, and they were stirred at room temperature overnight. The solvent was evaporated, and the obtained crude product was dissolved in 5 ml of ethanol. 0.2 g of 10% palladium/carbon was added to the solution, and they were stirred in the presence of hydrogen at room temperature overnight. After the filtration through Celite, the solvent was evaporated, and the obtained crude product was dissolved in 5 ml of concentrated hydrochloric acid. The obtained solution was stirred at 80° C. for 1.5 hours. The solvent was evaporated, and the obtained crude product was treated in the same manner as that in Step 11 in Example 1 to obtain the title compound.

(4S)-5-(5-Amidino-2-(2-(diethoxyphosphoryl)ethyl)phenoxy)-4-((1-(1-pyridine-4-yl)piperidine-4-carbonyl)amino)pentanoic acid bistrifluoroacetate:

Yield: 26.7 mg (0.032 mmol) (4.5%) H-NMR (DMSO-d6) δ 1.23 (6H, br), 1.50–2.10 (6H, m), 2.30 (2H, br), 2.55–3.15 (6H, m), 3.15–4.30 (12H, m), 7.20 (2H, br), 7.37–7.57 (2H, m), 8.10 (1H, br), 8.20 (2H, br), 9.10 (2H, br), 9.20 (2H, br), 9.40 (1H, br).

(4S)-5-(5-Amidino-2-(2-(ethoxy(hydroxy)phosphoryl)ethyl)-phenoxy)-4-((1-(1-pyridine-4-yl)piperidine-4-carbonyl)amino)pentanoic acid bistrifluoroacetate:

Yield: 25.5 g (0.032 mmol) (4.5%) H-NMR (DMSO-d6) δ 1.19 (3H, t), 1.60 (2H, br), 1.80–2.00 (4H, m), 2.30 (2H, br), 2.58–2.95 (4H, m), 3.00–4.30 (10H, m), 7.18 (2H, d), 7.38 (2H, m), 8.06 (1H, d), 8.20 (2H, d), 9.04 (2H, br), 9.23 (3H, br).

Step 5: Synthesis of (4S)-5-(5-amidino-2-(2-phosphorylethyl)phenoxy)-4-((1-(1-pyridine-4-yl)piperidine-4-carbonyl)-amino)pentanoic acid bistrifluoroacetate 23 mg (0.029 mmol) of (4S)-5-(5-amidino-2-(2-(ethoxy(hydroxy) phosphoryl)ethyl)phenoxy)-4-((1-(1-pyridine-4-yl)piperidine-4-carbonyl)amino)pentanoic acid bistrifluoroacetate obtained in step 4 was dissolved in 5 ml of dioxane. 0.03 ml (0.23 mmol) of trimethylsilyl bromide was added to the obtained solution, and they were stirred at room temperature for 3 days. The solvent was evaporated, and the obtained crude product was treated in the same manner as that in Step 11 in Example 1 to obtain the title compound.

Yield: 10 mg (0.013 mmol) (44%) MS (ESI, m/z) 548 (MH+) H-NMR (DMSO-d6) δ 1.60 (2H, br), 1.70–2.00 (4H, m), 2.30 (2H, br), 2.70 (2H, br), 2.90 (2H, br), 3.20 (2H, br), 3.40–4.30 (6H, m), 7.17 (2H, d), 7.37 (2H, m), 8.16 (1H, d), 8.20 (2H, d), 9.19 (2H, br), 9.25 (2H, br).

EXAMPLE 5

[2-(4-Hydroxylamidino-2-[2-[(1-(1-pyridine-4-yl)piperidine-4-carbonyl)amino]ethoxy]phenyl)ethyl] phosphoric acid bistrifluoroacetate

Step 1: Synthesis of diethyl [2-(4-cyano-2-[2-[(1-(1-pyridine-4-yl)piperidine-4-carbonyl)amino]ethoxy]phenyl)vinyl]phosphate bistrifluoroacetate 1 g (2.36 mmol) of diethyl[2-[(2-(2-t-butoxycarbonyl-amino)ethoxy)-4-cyano-phenyl]vinyl]phosphate was dissolved in a mixture of 15 ml of dioxane and 15 ml of 4 N solution of hydrogen chloride in dioxane, and the obtained solution was stirred at room temperature for 2 hours. The solvent was evaporated, and the obtained crude product was dissolved in 30 ml of N,N-dimethylformamide (dehydrated). 540 mg (2.60 mmol) of 1-(4-pyridyl)-4-piperidinecarboxylic acid hydrochloride, 520 mg (3.07 mmol) of 2-chloro-1,3-dimethylimidazonium chloride and 2 ml (14.2 mmol) of triethylamine were added to the obtained solution, and they were stirred overnight. The solvent was evaporated, and the obtained crude product was treated in the same manner as that in Step 11 in Example 1 to obtain the title compound.

Yield: 1.20 g (1.91 mmol) (81%) MS (ESI, m/z) 513 (MH+) H-NMR (DMSO-d6) δ 1.25 (6H, t), 1.60 (2H, br), 1.90 (2H, br), 2.60 (2H, br), 3.20 (2H, br), 3.50 (2H, br), 4.00 (4H, q), 4.20 (3H, br), 6.75 (1H, t), 7.19 (2H, d), 7.46 (1H, d), 7.53–7.68 (2H, m), 7.92 (1H, d), 8.15 (1H, br), 8.21 (2H, d).

Step 2 Synthesis of diethyl [2-(4-cyano-2-[2-[(1-(1-pyridine-4-yl)piperidine-4-carbonyl)amino]ethoxy]phenyl)ethyl]phosphate mono-trifluoroacetate 1.2 g (1.91 mmol) of diethyl [2-(4-cyano-2-[2-[(1-(1-pyridine-4-yl)piperidine-4-carbonyl)amino]ethoxy]phenyl)vinyl]phosphate mono-trifluoroacetate obtained in step 1 was dissolved in 10 ml of ethanol. 0.12 g of 10% palladium/carbon was added to the obtained solution, and they were stirred in the presence of hydrogen at room temperature overnight. After the filtration through Celite, the solvent was evaporated, and the obtained crude product was treated in the same manner as that in Step 11 in Example 1 to obtain the title compound.

Yield: 259 mg (0.41 mmol) (22%) MS (ESI, m/z) 515 (MH+)

Step 3 Synthesis of monoethyl [2-(4-hydroxyamidino-2-[2-[(1-(1-pyridine-4-yl)piperidine-4-carbonyl)amino]ethoxy]phenyl)ethyl]-phosphate bistrifluoroacetate Synthesis of [2-(4-hydroxyamidino-2-[2-[(1-(1-pyridine-4-yl)piperidine-4-carbonyl)amino]ethoxy]phenyl)ethyl] phosphoric acid bistrifluoroacetate:

129 mg (0.206 mmol) of diethyl[2-(4-cyano-2-[2-[(1-(1-pyridine-4-yl)piperidine-4-carbonyl)amino]ethoxy]phenyl)ethyl]phosphate mono-trifluoroacetate obtained in Step 2 was dissolved in 5 ml of ethanol. 22 mg (0.31 mmol) of hydroxylamine hydrochloride and 0.05 ml (0.31 mmol) of triethylamine were added to the obtained solution, and they were stirred at 80° C. for 4 hours. The solvent was evaporated, 5 ml of concentrated hydrochloric acid was added to the obtained crude product, and they were stirred at 80° C. for 4 hours. The solvent was evaporated, and the obtained crude product was treated in the same manner as that in Step 11 in Example 1 to obtain the title compound.
Monoethyl [2-(4-hydroxyamidino-2-[2-[(1-(1-pyridine-4-yl)piperidine-4-carbonyl)amino]ethoxy]phenyl)ethyl] phosphate bistrifluoroacetate:

Yield: 31.4 mg (0.042 mmol) (20%) MS (ESI, m/z) 520 (MH+) H-NMR (DMSO-d6) δ 1.20 (3H, t), 1.50–1.70 (2H, m), 1.80–2.00 (4H, m), 2.55–2.70 (2H, m), 2.75–2.90 (2H, m), 3.20 (2H, br), 3.50 (2H, br), 3.95 (2H, q), 4.10 (2H, br), 4.20 (1H, br), 7.17–7.26 (3H, m), 7.39 (2H, d), 8.20–8.30 (4H, m).

[2-(4-Hydroxylamidino-2-[2-[(1-(1-pyridine-4-yl)piperidine-4-carbonyl)amino]ethoxy]phenyl)ethyl] phosphoric acid bistrifluoroacetate:

Yield: 4.9 mg (0.007 mmol) (3%) MS (ESI, m/z) 492 (MH+) H-NMR (DMSO-d6) δ 1.58 (2H, br), 1.80–1.83 (4H, m), 2.63 (2H, br), 2.80 (2H, br), 3.10–4.00 (4H, m), 4.05 (2H, br), 4.15 (1H, br), 7.15-7.23 (3H, m), 7.32 (2H, d), 8.19 (2H, d), 8.29 (2H, br).

EXAMPLE 6

[2-(4-Hydroxylamidino-2-[2-[4-(1-pyrrolidinecarbamoyl)benzoylamino]ethoxy]phenyl)ethyl]phosphoric acid monotrifluoroacetate Step 1: Synthesis of diethyl [2-(4-cyano-2-[2-[4-(1-pyrrolidinecarbamoyl)benzoylamino]ethoxy]phenyl)ethyl]phosphate mono-trifluoroacetate 0.88 g (1.67 mmol) of diethyl [2-(4-cyano-2-[2-[4-(1-pyrrolidinecarbamoyl)benzoylamino]ethoxy]phenyl)vinyl]phosphate obtained in the same manner as that in Step 1 in Example 3 was dissolved in 10 ml of ethanol. 0.1 g of 10% palladium/carbon was added to the obtained solution, and they were stirred in the presence of hydrogen at room temperature overnight. After the filtration through Celite, the solvent was evaporated, and the obtained crude product was treated in the same manner as that in Step 11 in Example 1 to obtain the title compound.

Yield: 692 mg (0.31 mmol) (78%) MS (ESI, m/z) 528 (MH+)

Step 2: Synthesis of monoethyl [2-(4-hydroxylamidino-2-[2-[4-(1-pyrrolidinecarbamoyl)benzoylamino]ethoxy]phenyl)vinyl]phosphate mono-trifluoroacetate Synthesis of [2-(4-hydroxylamidino-2-[2-[4-(1-pyrrolidinecarbamoyl)benzoylamino]ethoxy]phenyl)vinyl] phosphoric acid mono-trifluoroacetate:

0.34 g (0.66 mmol) of diethyl [2-(4-cyano-2-[2-[4-(1-pyrrolidinecarbamoyl)benzoylamino]ethoxy]phenyl)ethyl] phosphate mono-trifluoroacetate obtained in step 1 was dissolved in 10 ml of ethanol. 70 mg (0.98 mmol) of hydroxylamine hydrochloride and 0.14 ml (0.98 mmol) of triethylamine were added to the obtained solution, and they were stirred at 80° C. for 5 hours. The solvent was evaporated. 5 ml of concentrated hydrochloric acid was added to the obtained crude product, and they were stirred at 80° C. for 2.5 hours. The solvent was evaporated, and the residue was treated in the same manner as that in Step 11 in Example 1 to obtain the title compound.
Monoethyl[2-(4-hydroxylamidino-2-[2-[4-(1-pyrrolidinecarbamoyl)-benzoylamino]ethoxy]phenyl)vinyl] phosphate mono-trifluoroacetate:

Yield: 103.5 mg(0.16 mmol)(24%) MS (ESI, m/z) 533 (MH+) H-NMR (DMSO-d6) δ 1.16 (3H, t), 1.75–2.00 (6H, m), 2.85 (2H, br), 3.35 (2H, t), 3.50 (2H, t), 3.70 (2H, br), 3.88 (2H, q), 4.25 (2H, br), 7.25 (1H, d), 7.30 (1H, s), 7.39 (1H, d), 7.58 (2H, d), 7.91 (2H, d), 8.90 (2H, br).
[2-(4-Hydroxylamidino-2-[2-[4-(1-pyrrolidinecarbamoyl)benzoylamino]-ethoxy]phenyl)vinyl]phosphoric acid mono-trifluoroacetate:

Yield: 46.32 mg (0.075 mmol) (11%) MS (ESI, m/z) 505 (MH+) H-NMR (DMSO-d6) δ 1.75–2.00 (6H, m), 2.88 (2H, br), 3.35 (2H, t), 3.50 (2H, t), 3.75 (2H, br), 4.25 (2H, br), 7.24 (1H, d), 7.31 (1H, s), 7.37 (1H, d), 7.91–8.00 (2H, m), 8.96 (2H, m).

EXAMPLE 7

Determination of Activity of Inhibiting the Activated Blood-coagulation Factor X 130 μl of 100 mM tris hydrochloride buffer adjusted to pH 8.4 was added to 10 μl of an aqueous solution of a compound to be tested. Then 10 μl of a 0.5 unit/ml solution of activated human blood coagulation factor X (a product of Enzyme Research Co.) in tris hydrochloride buffer of pH 8.4 was added to the resultant mixture. After the incubation at room temperature for 10 minutes, 50 μl of a solution of N-benzoyl-L-isoleucine-L-glutamine-glycine-L-arginine-P-nitroanilide hydrochloride (a product of Peptide Institute Inc.) adjusted to 0.8 mM with tris hydrochloride (pH 8.4) was added thereto. The absorbance was determined and then the initial reaction rate was determined. A control was prepared in the same manner as that described above except that the solution of the compound to be tested was replaced with 10 μl of tris hydrochloride buffer adjusted to pH 8.4. The absorbance was determined with MICROPLATE READER Model 3550-UV (a product of BIO RAD) at a wave length of 405 nm at intervals of 15 seconds for 16 minutes. The negative logarithm ($pIC_{50}$) of a concentration of the test compound which inhibits 50% of the activity (initial rate) of the activated blood coagulation factor X in the absence of the test compound was determined, and employed as the index of the activity of inhibiting activated blood coagulation factor X.

The activities, of inhibiting activated blood coagulation factor X, of typical compounds are shown in Table 1 given below.

EXAMPLE 8

Determination of Thrombin-Inhibiting Activity

130 μl of 100 mM tris hydrochloride buffer adjusted to pH 8.4 was added to 10 μl of an aqueous solution of a test compound. Then 10 μl of a solution of human thrombin (a product of SIGMA Co.) adjusted to 2 units/ml with tris hydrochloride buffer of pH 8.4 was added to the resultant mixture. After the incubation at room temperature for 10 minutes, 50 μl of a solution of D-phenylalanine-L-pipecolyl-L-arginine-P-nitroanilide dihydrochloride (S-2238; a product of Daiichi Kagaku Yakuhin Co.) adjusted to 0.4 mM with tris hydrochloride buffer of pH 8.4 was added thereto. The absorbance was determined and then the initial reaction rate was determined. A control was prepared in the same manner as that described above except that the solution of the compound to be tested was replaced with 10 μl of tris hydrochloride buffer adjusted to pH 8.4. The absorbance was determined with MICROPLATE READER Model 3550-UV (a product of MIO RAD) at a wave length of 405 nm at intervals of 15 seconds for 16 minutes. The negative logarithm ($pIC_{50}$) of a concentration of the test compound which inhibits 50% of the activity (initial rate) of the thrombin in the absence of the test compound was determined, and employed as the index of the activity of inhibiting thrombin.

The activities, of inhibiting thrombin, of typical compounds are shown in Table 1 given below.

EXAMPLE 9

Determination of Blood Anticoagulating Activity

The blood anticoagulating activity was determined by a prothrombin time (PT) determination method. The PT was determined as follows: The blood was taken from healthy people. 3.8% aqueous trisodium citrate solution was added to the blood in a volume ratio of 1:10. The blood plasma was separated by the centrifugation. 5 μl of DMSO solution containing a test compound was added to 45 μl of the blood plasma. After the incubation at room temperature for 2 minutes, a test tube containing the blood plasma solution was placed in Sysmex CA-3000 fully automatic blood coagulation determination device (a product of Toa Medical Electronics Co., Ltd.), and incubated at 37° C. for 3 minutes. 100 μl of Sysmex PT II (rabbit brain tissue thromboplastin, 13.2 mM calcium chloride; a product of Toa Medical Electronics Co., Ltd.) was fed into the test tube. PT was automatically determined with the device. A sample containing 5 μl of DMSO in place of the solution of the test compound was used as the control. The negative logarithm (pPT2) of the concentration of the test compound which elongated PT of the control to the twice as long was determined, and employed as the index of the blood anticoagulating activity.

TABLE 1

| | Activity of inhibiting activated blood coagulation factor X ($pIC_{50}$) | Thrombin-inhibiting activity ($pIC_{50}$) |
|---|---|---|
| Compd. of Ex. 1 | 8.5 | <3.5 |
| Compd. of Ex. 2 | 8.6 | <4.0 |
| Compd. of Ex. 3 | 8.6 | 4.4 |
| Compd. of Ex. 4 | 8.7 | <4.0 |
| Compd. of Ex. 6 | 7.1 | <4.0 |
| Compd. of Ex. 46 of WO 9964392 | 7.4 | 3.9 |
| Compd. of Ex. 47 of WO 9964392 | 6.9 | 4.3 |

It is apparent from the results that the compound in Example 1 [compound of formula (2-1)] also had a high activity of inhibiting the blood coagulation (pPT2=6.8).

From the results, it was understood that the benzamidine derivatives of the present invention exhibit a high activity of specifically inhibiting activated blood coagulation factor X, and they exhibit a high anticoagulating activity based on this inhibiting activity.

The structural formulae of the compounds of the present invention described in the Examples are given below.

Compound of Example 1

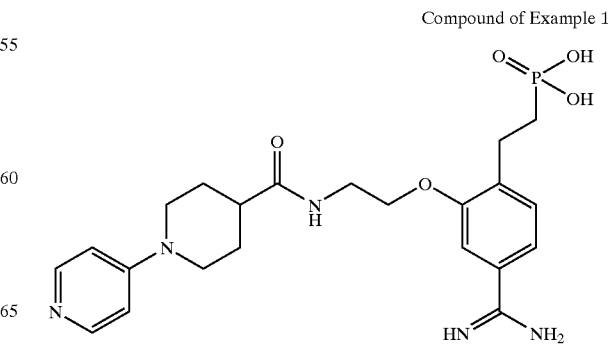

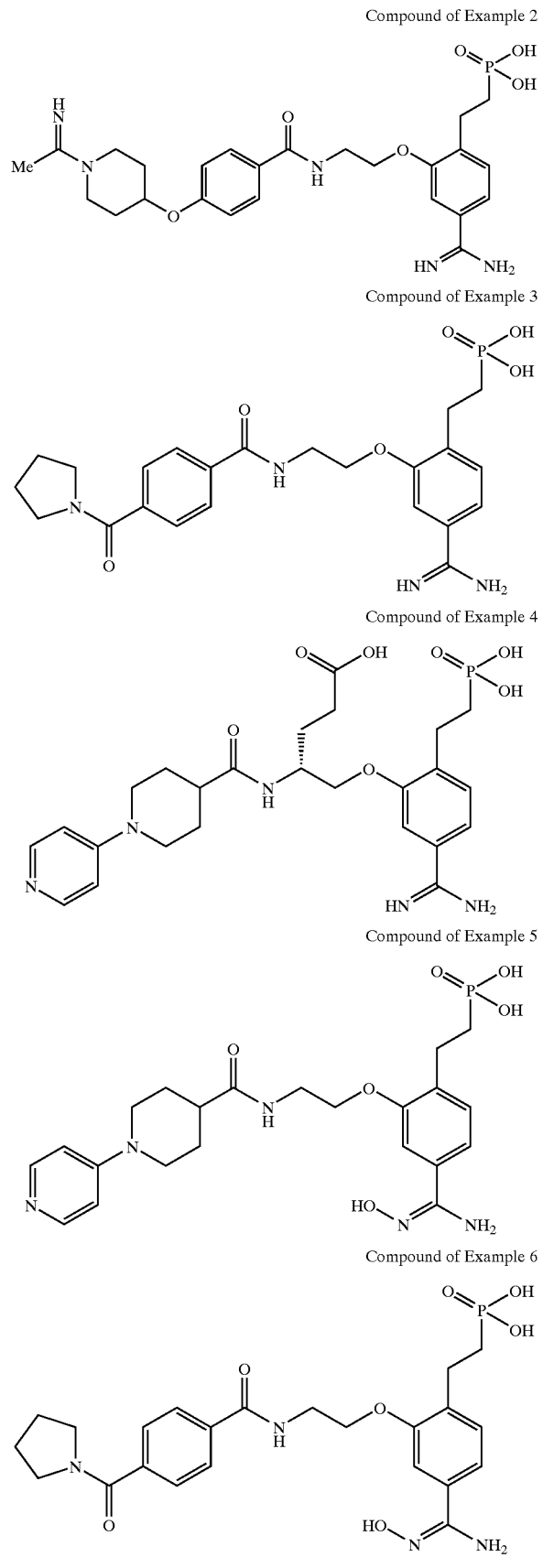

Compound of Example 2

Compound of Example 3

Compound of Example 4

Compound of Example 5

Compound of Example 6

The anticoagulant containing a compound of the present invention or a salt thereof as the active ingredient has a blood-coagulation inhibiting effect based on the excellent effect of inhibiting activated blood-coagulation factor X. Therefore, the compounds of the present invention are usable as agents for preventing or treating diseases, for example, cerebrovascular disorders such as cerebral infarction, cerebral stroke, cerebral thrombosis, cerebral embolism, transient ischemic attack (TIA) and subarachnoidal hemorrhage (vasospasm); ischemic heart diseases such as acute and chronic myocardial infarction, unstable angina and coronary thrombolysis; pulmonary vascular disorders such as pulmonary infarction and pulmonary embolism; peripheral occlusion; deep vein thrombosis; disseminated intravascular coagulation; thrombus formation after an artificial blood vessel-forming operation or artificial valve substitution; re-occlusion and re-stenosis after a coronary bypass-forming operation; re-occlusion and re-stenosis after reconstructive operation for the blood circulation such as percutaneous transluminal coronary angioplasty (PTCA) or percutaneous transluminal coronary recanalization (PTCR); and thrombus formation in the course of the extracorporeal circulation.

What is claimed is:

1. A benzamidine compound of formula (1) or a pharmaceutically acceptable salt thereof:

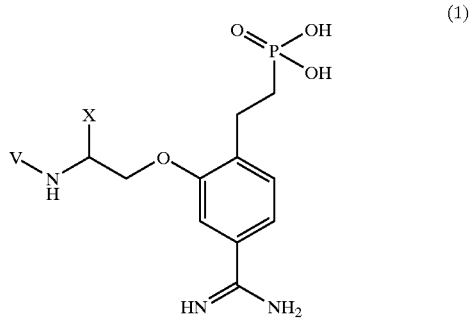

(1)

wherein X represents a hydrogen atom, a carboxyl group, an alkoxycarbonyl group having 2 to 4 carbon atoms, an alkyl group having 1 to 3 carbon atoms, which may have a substituent(s), or a benzyl group which may have a substituent(s); the substituent(s) being a carboxyl group or alkoxycarbonyl groups having 2 to 8 carbon atoms, V represents a benzoyl group which may have a substituent(s) or a piperidinecarbonyl group which may have a substituent(s); wherein said substituent(s) on said benzoyl group or said piperidinecarbonyl group is selected from the group consisting of iminoalkylpiperidyloxy groups having 7 to 10 carbon atoms, aryl groups having 6 to 10 carbon atoms, heteroaryl groups having 4 to 5 carbon atoms, carbamoyl group, and mono- and dialkylcarbamoyl groups having 2 to 7 carbon atoms, wherein two alkyl groups in each of the dialkylcarbamoyl groups may be bonded to each other to form a ring selected from 1-pyrrolidincarbonyl group, 1-piperidinecarbonyl group, 1-piperazinecarbonyl group and 1-morpholinecarbonyl group and R represents a hydrogen atom, a hydroxyl group, an alkoxyl group, an amino group, a carboxyl group, an alkoxycarbonyl group, an alkylsulfonyl group, a carbamoyl group, a carbamoyl group in which one or two hydrogens are replaced with an alkyl group, a formyl group, an acyl group, or an alkylcarboxyl group.

2. The benzamidine compound or pharmaceutically acceptable salt thereof according to claim 1, wherein, in formula (1), V represents a benzoyl or piperidinecarbonyl group which may have a substituent(s); the substituent(s) being selected from the group consisting of iminoalkylpiperidyloxy groups having 7 to 10 carbon atoms, aryl groups having 6 to 10 carbon atoms and heteroaryl groups having 4 to 5 carbon atoms.

3. The benzamidine compound or pharmaceutically acceptable salt thereof according to claim 1, wherein, in formula (1), X represents a hydrogen atom, a carboxymethyl group or carboxyethyl group.

4. The benzamidine compound or pharmaceutically acceptable salt thereof according to claim 2, wherein, in formula (1), X represents a hydrogen atom, a carboxymethyl group or carboxyethyl group.

5. The benzamidine compound or pharmaceutically acceptable salt thereof according to claim 1, wherein, in formula (1), V represents a 1-acetimidoyl-4-piperidyloxybenzoyl group, 1-(4-pyridyl)-piperidine-4-carbonyl group or 4-(1-pyrrolidinecarbonyl)benzoyl group.

6. The benzamidine compound or pharmaceutically acceptable salt thereof according to claim 2, wherein, in formula (1), V represents a 1-acetimidoyl-4-piperidyloxybenzoyl group or 1-(4-pyridyl)-piperidine-4-carbonyl group.

7. The benzamidine compound or pharmaceutically acceptable salt thereof according to claim 2, which has the structure of formula (2-1):

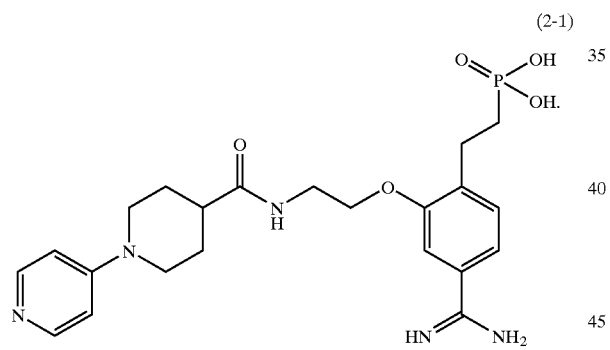

(2-1)

or a pharmaceutically acceptable salt thereof.

8. The benzamidine compound or pharmaceutically acceptable salt thereof according to claim 1, which has a structure of one of formulae (2—2) to (2-4):

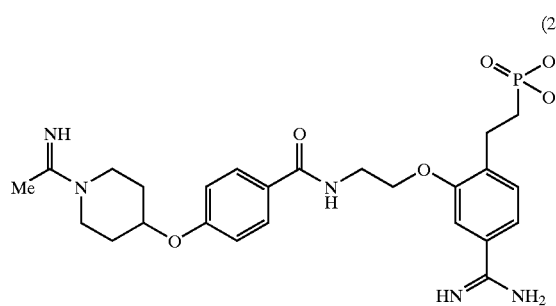

(2-2)

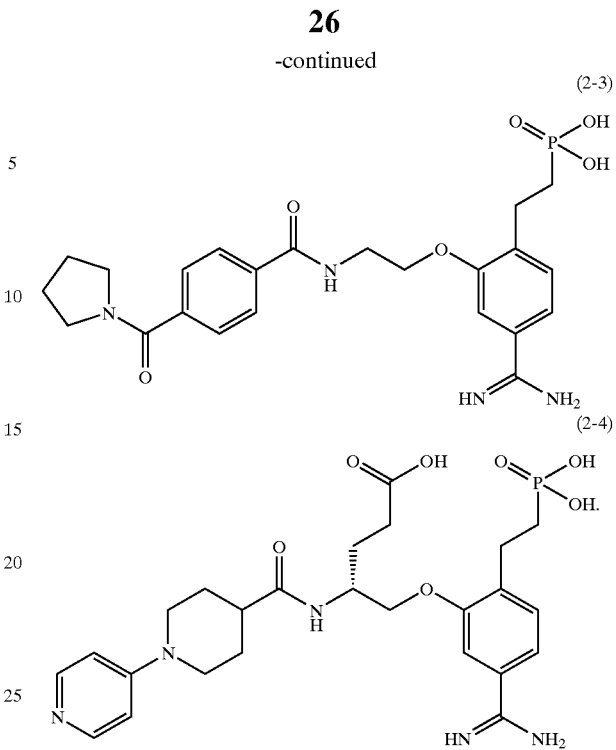

(2-3)

(2-4)

or a pharmaceutically acceptable salt thereof.

9. The benzamidine compound or pharmaceutically acceptable salt thereof according to claim 1, which has a structure of one of formulae (2-5) and (2-6):

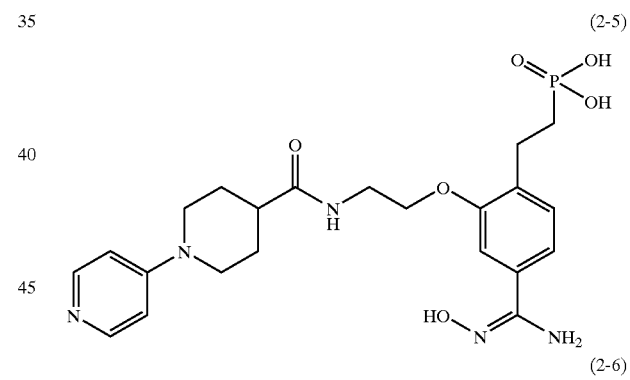

(2-5)

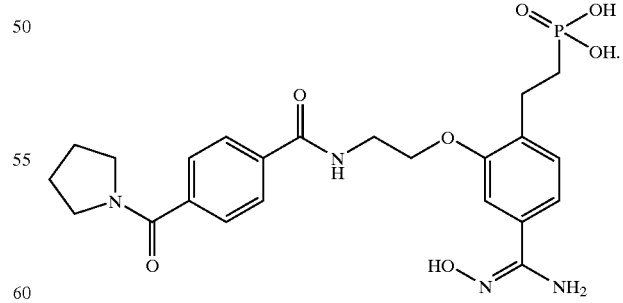

(2-6)

or a pharmaceutically acceptable salt thereof.

10. A pharmaceutical composition, comprising a therapeutically effective amount of a benzamidine compound or pharmaceutically acceptable salt thereof according to claim 1.

11. A pharmaceutical composition, comprising a therapeutically effective amount of a benzamidine compound or pharmaceutically acceptable salt thereof according to claim 2.

12. A pharmaceutical composition, comprising a therapeutically effective amount of a benzamidine compound or pharmaceutically acceptable salt thereof according to claim 3.

13. A pharmaceutical composition, comprising a therapeutically effective amount of a benzamidine compound or pharmaceutically acceptable salt thereof according to claim 4.

14. A pharmaceutical composition, comprising a therapeutically effective amount of a benzamidine compound or pharmaceutically acceptable salt thereof according to claim 5.

15. A pharmaceutical composition, comprising a therapeutically effective amount of a benzamidine compound or pharmaceutically acceptable salt thereof according to claim 6.

16. A pharmaceutical composition, comprising a therapeutically effective amount of a benzamidine compound or pharmaceutically acceptable salt thereof according to claim 7.

17. A pharmaceutical composition, comprising a therapeutically effective amount of a benzamidine compound or pharmaceutically acceptable salt thereof according to claim 8.

18. A pharmaceutical composition, comprising a therapeutically effective amount of a benzamidine compound or pharmaceutically acceptable salt thereof according to claim 9.

19. A method of treating thrombosis or embolism, which comprises administering a pharmaceutical composition according to claim 10 to a patient in need thereof.

20. A method of treating thrombosis or embolism, which comprises administering a pharmaceutical composition according to claim 16 to a patient in need thereof.

21. A method of treating thrombosis or embolism, which comprises administering a pharmaceutical composition according to claim 17 to a patient in need thereof.

22. A method of treating thrombosis or embolism, which comprises administering a pharmaceutical composition according to claim 18 to a patient in need thereof.

23. A method of treating diseases caused by peripheral embolism, deep vein thrombosis, disseminated intravascular coagulation, thrombus formation after an artificial blood vessel-forming operation or artificial valve substitution, re-occlusion and re-stenosis after a coronary bypass-forming operation, re-occlusion and re-stenosis after reconstructive operation for the blood circulation, and thrombus formation in the course of the extracorporeal circulation, which comprises the step of administering the pharmaceutical composition according to claim 10 to a subject in need thereof.

24. A method of treating diseases caused by peripheral embolism, deep vein thrombosis, disseminated intravascular coagulation, thrombus formation after an artificial blood vessel-forming operation or artificial valve substitution, re-occlusion and re-stenosis after a coronary bypass-forming operation, re-occlusion and re-stenosis after reconstructive operation for the blood circulation, and thrombus formation in the course of the extracorporeal circulation, which comprises the step of administering the pharmaceutical composition according to claim 16 to a subject in need thereof.

25. A method of treating diseases caused by peripheral embolism, deep vein thrombosis, disseminated intravascular coagulation, thrombus formation after an artificial blood vessel-forming operation or artificial valve substitution, re-occlusion and re-stenosis after a coronary bypass-forming operation, re-occlusion and re-stenosis after reconstructive operation for the blood circulation, and thrombus formation in the course of the extracorporeal circulation, which comprises the step of administering the pharmaceutical composition according to claim 17 to a subject in need thereof.

26. A method of treating diseases caused by peripheral embolism, deep vein thrombosis, disseminated intravascular coagulation, thrombus formation after an artificial blood vessel-forming operation or artificial valve substitution, re-occlusion and re-stenosis after a coronary bypass-forming operation, re-occlusion and re-stenosis after reconstructive operation for the blood circulation, and thrombus formation in the course of the extracorporeal circulation, which comprises the step of administering the pharmaceutical composition according to claim 18 to a subject in need thereof.

27. A method of treating cerebral infarction or cerebral stroke, which comprises administering a pharmaceutical composition according to claim 10 to a patient in need thereof.

28. A method of treating cerebral infarction or cerebral stroke, which comprises administering a pharmaceutical composition according to claim 16 to a patient in need thereof.

29. A method of treating cerebral infarction or cerebral stroke, which comprises administering a pharmaceutical composition according to claim 17 to a patient in need thereof.

30. A method of treating cerebral infarction or cerebral stroke, which comprises administering a pharmaceutical composition according to claim 18 to a patient in need thereof.

* * * * *

UNITED STATES PATENT AND TRADEMARK OFFICE
CERTIFICATE OF CORRECTION

PATENT NO. : 6,784,191 B2
DATED : August 31, 2004
INVENTOR(S) : Yoshida et al.

It is certified that error appears in the above-identified patent and that said Letters Patent is hereby corrected as shown below:

Title page,
Items [45] and [*] Notice, should read as follows:
-- [45] **Date of Patent: *Aug. 31, 2004**
  [*]   Notice: Subject to any disclaimer, the term of this patent is extended or adjusted under 35 U.S.C. 154(b) by 0 days.
This Patent is subject to a terminal disclaimer. --

Signed and Sealed this

Seventh Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 6,784,191 B2
DATED : August 31, 2004
INVENTOR(S) : Kaoru Yoshida et al.

It is certified that error appears in the above-identified patent and that said Letters Patent is hereby corrected as shown below:

Column 24,
Lines 26-39, Formula (I) reading

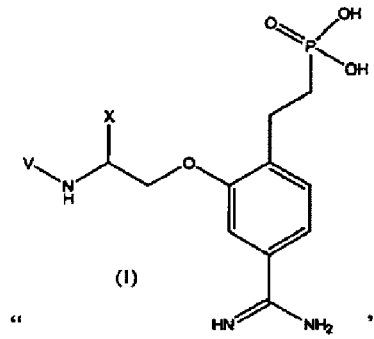 " should read as -- 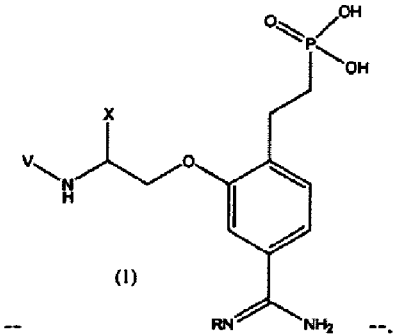 --.

Signed and Sealed this

Fifteenth Day of March, 2005

JON W. DUDAS
*Director of the United States Patent and Trademark Office*